(12) United States Patent
Jennfors

(10) Patent No.: US 12,377,237 B2
(45) Date of Patent: Aug. 5, 2025

(54) BREATHING PROTECTOR

(71) Applicant: Coloplast A/S, Humlebaek (DK)

(72) Inventor: Peter Jennfors, Malmo (SE)

(73) Assignee: Coloplast A/S, Humlebaek (DK)

( * ) Notice: Subject to any disclaimer, the term of this patent is extended or adjusted under 35 U.S.C. 154(b) by 786 days.

(21) Appl. No.: 17/431,172

(22) PCT Filed: Feb. 13, 2020

(86) PCT No.: PCT/EP2020/053816
§ 371 (c)(1),
(2) Date: Aug. 15, 2021

(87) PCT Pub. No.: WO2020/165373
PCT Pub. Date: Aug. 20, 2020

(65) Prior Publication Data
US 2022/0143354 A1 May 12, 2022

(30) Foreign Application Priority Data

Feb. 15, 2019 (SE) .................................. 1950189-9

(51) Int. Cl.
*A61M 16/10* (2006.01)
*A61M 16/04* (2006.01)

(52) U.S. Cl.
CPC .... *A61M 16/1045* (2013.01); *A61M 16/0468* (2013.01); *A61M 16/047* (2013.01); *A61M 16/105* (2013.01)

(58) Field of Classification Search
CPC .............. A61M 16/00; A61M 16/0468; A61M 16/047; A61M 16/1045; A61M 16/105; A61M 16/1055; A61M 2205/7545

(Continued)

(56) References Cited

U.S. PATENT DOCUMENTS 3,342,200 A * 9/1967 Wilcox ................. F16K 15/148
137/854
5,487,382 A 1/1996 Bezicot
(Continued)

FOREIGN PATENT DOCUMENTS

DE 202011003781 U1 5/2011
DE 202012001825 U1 4/2012
(Continued)

OTHER PUBLICATIONS

Swedish Search Report dated Sep. 6, 2019 related to corresponding Swedish Patent Application No. 1950189-9.
(Continued)

*Primary Examiner* — Tu A Vo
(74) *Attorney, Agent, or Firm* — Coloplast Corp., Coloplast A/S; Nick Baumann

(57) ABSTRACT

A breathing protector for use in a stoma of a laryngectomized or tracheotomised person is described. The breathing protector includes at least one inlet, at least one outlet, a heat and moisture exchanger (HME) and an air filter, such that an air flow will pass through the HME and the air filter when the air flow passes through the inlet to the outlet. A housing is provided with an upper part and a lower part. According to an example, the inlet is provided in the upper part and the outlet is provided in the lower part. The upper part is provided with a closing member that when activated closes the communication between the inlet and the outlet via a closing valve.

21 Claims, 2 Drawing Sheets

(58) Field of Classification Search
USPC .................................................. 251/318–334
See application file for complete search history.

(56) References Cited

U.S. PATENT DOCUMENTS

| | | | | |
|---|---|---|---|---|
| 5,590,644 | A * | 1/1997 | Rosenkoetter | A61M 16/1045 128/205.12 |
| 5,666,950 | A | 9/1997 | Smith | |
| 5,738,095 | A * | 4/1998 | Persson | A61M 16/0468 128/207.14 |
| 5,964,416 | A * | 10/1999 | Jaeger | A61M 15/0065 222/402 |
| 6,202,877 | B1 * | 3/2001 | La Torre | A47G 19/2272 220/254.1 |
| 6,422,235 | B1 * | 7/2002 | Persson | A61F 2/20 128/200.26 |
| 8,051,856 | B2 * | 11/2011 | Bare | A61M 16/208 128/207.14 |
| 8,505,537 | B2 | 8/2013 | Persson | |
| 9,084,860 | B2 * | 7/2015 | Leibitzki | A61M 16/1045 |
| 9,427,542 | B2 * | 8/2016 | Persson | A61M 16/1045 |
| 10,335,269 | B2 * | 7/2019 | Fahl | A61M 16/0468 |
| 10,390,942 | B2 * | 8/2019 | Fahl | A61F 2/20 |
| 10,464,722 | B2 * | 11/2019 | Cudworth | A47G 19/2266 |
| 10,478,287 | B2 * | 11/2019 | Fahl | A61F 2/20 |
| 11,878,121 | B2 * | 1/2024 | Fahl | A61M 16/201 |
| 2005/0178390 | A1 | 8/2005 | Worthington | |
| 2010/0288284 | A1 | 11/2010 | Persson | |
| 2011/0220108 | A1 | 9/2011 | Persson | |
| 2012/0090621 | A1 * | 4/2012 | van der Houwen | A61M 16/0468 128/207.16 |
| 2013/0192602 | A1 | 8/2013 | Leibitzki et al. | |
| 2013/0239958 | A1 | 9/2013 | Persson | |
| 2014/0150779 | A1 | 6/2014 | Persson | |
| 2015/0083119 | A1 * | 3/2015 | Persson | A61M 16/0468 128/201.13 |
| 2016/0256649 | A1 | 9/2016 | Hesselmar et al. | |
| 2016/0354569 | A1 | 12/2016 | Fahl | |
| 2018/0071083 | A1 | 3/2018 | Fahl | |
| 2020/0188620 | A1 * | 6/2020 | Markwardt | A61F 2/203 |

FOREIGN PATENT DOCUMENTS

| | | | | |
|---|---|---|---|---|
| DE | 202013008092 | U1 | 10/2013 | |
| DE | 102014002064 | B3 * | 6/2015 | A61F 2/20 |
| WO | WO-11144237 | A1 | 11/2011 | |
| WO | WO-2014060242 | A1 * | 4/2014 | A61F 2/20 |
| WO | WO-2015052121 | A1 * | 4/2015 | A61M 16/0468 |
| WO | WO-15124278 | A1 | 8/2015 | |

OTHER PUBLICATIONS

English abstract for DE-202013008092.
English abstract for DE-202012001825.

* cited by examiner

BREATHING PROTECTOR

CROSS-REFERENCE TO RELATED APPLICATIONS

This application claim priority to International Patent Application No. PCT/EP2020/053816 filed Feb. 13, 2020, and to Sweden Patent Application SE 1950189-9 filed Feb. 15, 2019, the contents of each of which is hereby incorporated by reference in its entirety.

TECHNICAL FIELD

This invention pertains in general to the field of a breathing protector for use in a stoma of a laryngectomized or tracheotomised person, said breathing protector having at least one inlet and at least one outlet, such that an air flow in use will pass from the surroundings of said person through said inlet to said outlet, into trachea of said person, said breathing protector comprising a heat and moisture exchanger (HME) and an air filter, such that said air flow will pass through said HME and said air filter when said air flow in use passes through said inlet to said outlet.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed, for example, when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air is controlled by means of a tracheostoma valve. In these situations, the valve can be arranged to remain open during breathing but can be closed to divert the airflow, through a small additional increase in exhaled air flow.

In this respect filter devices and breathing protectors have been developed to enable moisturizing of inhaled air and removal of small particles and bacteriological substances in said inhaled air. This is to resemble the functions of a nose. However, there are several complications related to the manufacturing of such devices. Firstly, the user of such devices is in need of good moisturizing and removal effect while keeping the size, such as the surface area, of the device as small as possible. Secondly, the moisturizing effect and removal effect is in need of large surface area, while not creating a too large resistance over the device. These criterions are contradictive, which the observant reader already has acknowledged. Also, a person with a laryngectomy has to hold his finger or thumb over these devices when wishing to speak, to thereby obstruct the air flow through the device and the stoma through the tracheal wall, which will burden the filter with undue contamination, due to transfer of impurities from the finger of the user to the filter.

U.S. Pat. No. 5,666,950 describes a device for filtering air that is to be breathed through a tracheostoma. This device comprises a pre-filter of electrostatically charged fibres, a first layer formed of activated carbon and a second layer of a hydrophilic material. The use of activated carbon provides filtration of small particles and absorption of gases, with a limited increase in the resistance to airflow through the device. However, the finger or thumb of the user will influence the antibacterilogical effect of the electrostatic filter in a negative way, since it is unreasonable to demand a totally bacteriological free condition of said finger or thumb, which means that said filter will be contaminated by time. Furthermore, the device according to U.S. Pat. No. 5,666,950 does only achieve an antibacteriological effect of approximately 50%, since the surface area of the electrostatic filter is restricted to the surface area of the opening communicating with the surroundings, while providing an adequate resistance over the device.

U.S. Pat. No. 5,487,382 describes an artificial nose with a housing and a hydrophilic filtering disc, further comprising a cap, which can be moved up and down to open/close windows in the housing. The artificial nose according to U.S. Pat. No. 5,487,382 has to be actively moved from an open position to a closed position and vice versa, and has a very limited antibacteriological effect.

U.S. Pat. No. 8,505,537 describes a breathing protector for use in a stoma of a laryngectomized or tracheotomised person. The breathing protector is provided with a closing member that may be activated to close the communication between said at least one inlet and said at least one outlet. The closing member is a member of, or attached to, a flexible cover. The resiliency of the flexible cover allows the flexible cover to be pressed down, inwardly, to closingly fit with a closing surface, such as a closing rib. A closing effect is obtained when the flexible cover is pressed against the closing rib.

Hence, an improved breathing protector would be advantageous and in particular a breathing protector which provides the possibility for a patient to close the breathing protector, such as during speech, with a low force. It would also be advantageous to obtain such a breathing protector, which provides tactile confirmation of a closing state, i.e. an open or a closed state, of the breathing protector. Furthermore, it would be advantageous to provide a breathing protector allowing for increased filtering effect and an excellent moisturizing effect, while still providing a small breathing protector with a satisfactory resistance over said breathing protector. It would also be advantageous to provide a breathing protector that is easily moved from an open to a closed state, which also provides the possibility to a patient to keep the breathing protector closed, such as during speech, without undue contamination of the filter by holding a finger or thumb over said opening during the entire period of speech.

SUMMARY

Accordingly, the present invention seeks to mitigate, alleviate or eliminate one or more of the above-identified deficiencies and to provide an improved breathing protector of the kind referred to. For this purpose the breathing protector has a housing which comprises of an upper part and a lower part, wherein at least one inlet is provided in said upper part of the housing and at least one outlet is provided in said lower part of the housing, and wherein a heat and moisture exchanger (HME) and an air filter are enclosed by said housing. The upper part of the housing is provided with a closing member that may be activated to close the communication between said at least one inlet and said at least one outlet via a closing valve proximally of the air filter.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a breathing protector and in particular to a breathing protector for use in a stoma of a laryngectomized or tracheotomised person, where said stoma is communicating with trachea of said person. However, the invention is not limited to this application but may be applied to other technical fields in which one wishes to remove particulate matter from an air stream while also moisturizing said air stream and providing the possibility to close said air stream.

Figure 1:
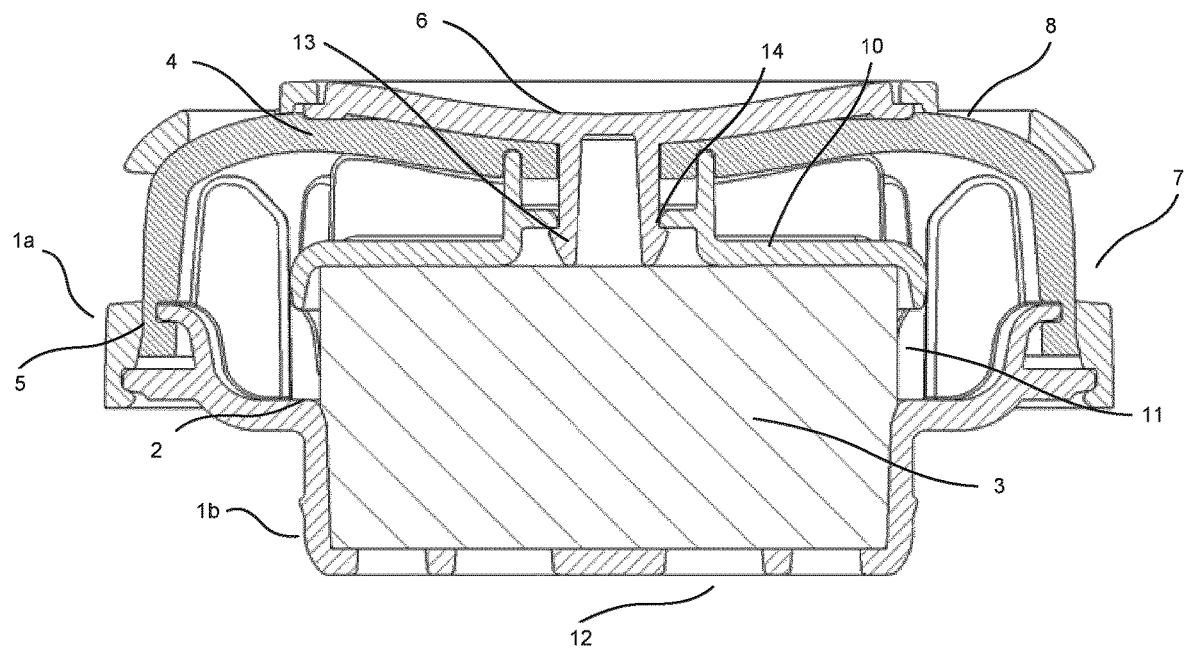
FIG. 1 is a cross sectional view of a breathing protector according to an embodiment of the present invention.
Figure 2:
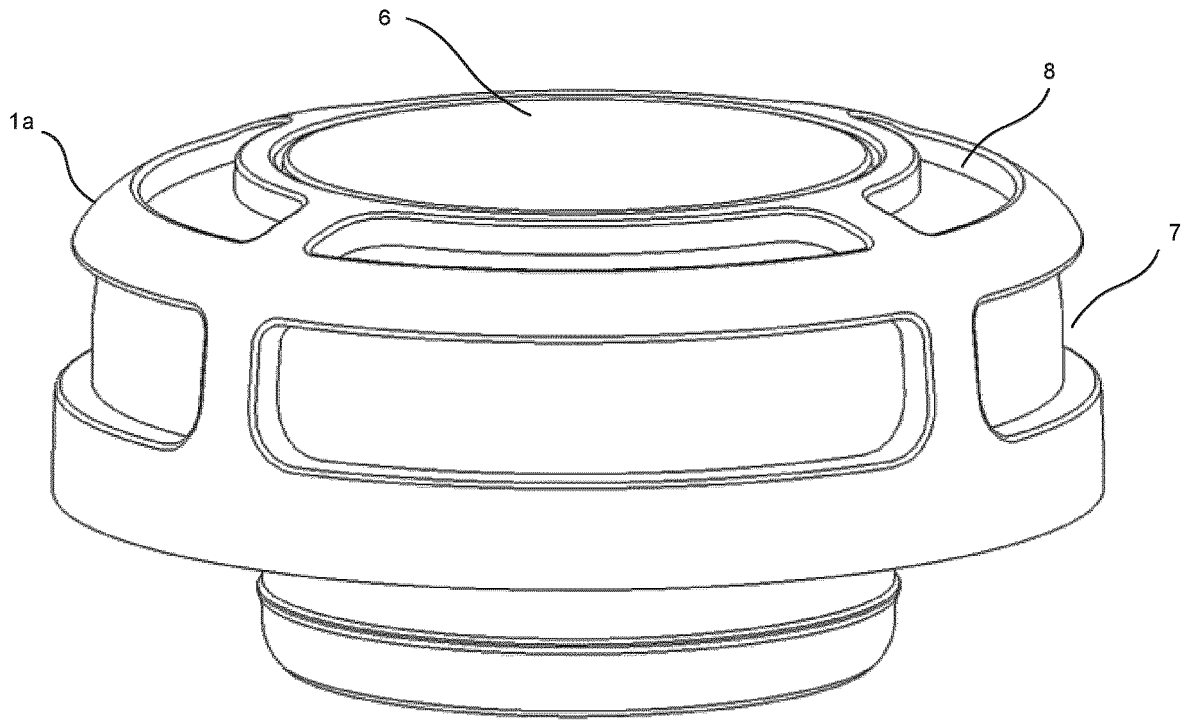
FIG. 2 is a perspective view of a breathing protector according to an embodiment of the present invention.

In an embodiment of the invention, which is illustrated in FIGS. 1 and 2, a breathing protector is provided. The breathing protector is for use in a stoma of a laryngectomized or tracheotomised person. Said breathing protector having at least one inlet and at least one outlet, such that an air flow in use will pass from the surroundings of said person through said inlet to said outlet, into trachea of said person. The breathing protector comprises a heat and moisture exchanger (HME) 3 and an air filter 4, such that said air flow will pass through said air filter 4 and said HME 3 when said air flow in use passes through said inlet to said outlet.

The air filter 4 is capable of filtering particulate matters, and in one embodiment, the air filter 4 is an electrostatic filter.

The breathing protector, illustrated in FIGS. 1 and 2, has a housing. Said housing comprises of an upper part 1a and a lower part 1b. The upper part 1a of the housing having at least one inlet 7, 8 and the lower part of the housing having at least one outlet 12. The HME 3 and the air filter 4 of the breathing protector are enclosed by said housing. Thus, when air is passing from the surroundings through the stoma, wherein or over which the breathing protector is arranged, the air passes in via the at least one first inlet 7, 8 of the upper part 1a of the housing, through the air filter 4 and the HME 3, into trachea of the patient through the at least one outlet 12 of the lower part 1b of the housing. As the air filter 4 and the HME 3 are enclosed by said housing, a minimized contamination of the air filter 4 may be assured and thus prolonging the filtering effect of the breathing protector, since the fingers and the neck of the user are prevented from coming in contact with the air filter 4.

With further reference to FIG. 1, the lower part 1b of the housing may have an accommodation, this accommodation may accommodate the HME 3. Accordingly, the HME 3 may be arranged in the lower part 1b of the housing. The air filter 4 may be arranged in the upper part 1a of the housing. Said air filter 4 may thus cover said at least one inlet 7, 8. Accordingly, when air is passing from the surroundings through the stoma, wherein or over which the breathing protector is arranged, the air passes in via the at least one inlet 7, 8 of the upper part 1a of the housing, through the air filter 4 and the HME 3 into trachea of the patient through the at least one outlet 12 of the lower part 1b of the housing.

As illustrated in FIG. 1, the upper part 1a of the housing is provided externally the air filter 4, which may be attached to, held by or integrated with, a rim 5. The upper part 1a of the housing is further provided with a closing member 6. The closing member 6 is not an integral part of the upper part of the housing 1a, but is separated from the upper part 1a of the housing. The closing member 6 is thus a separate closing member 6. The closing member 6 is preferably arranged centrally within the upper part 1b of the housing and can be activated to close the communication between said at least one inlet 7, 8 and said at least one outlet 12. The closing member 6 is positioned distally, i.e. away from the user, of the air filter 4. Accordingly, it may be possible to achieve a closing action by activating the closing member 6 instead of blocking airflow by holding a finger on the air filter 4 of the breathing protector. Thus, the air filter 4 may be relieved from undue contamination from the finger. The closure of the breathing protector is activated by the patient when the patient intends to speak. Furthermore, by the proposed breathing protector where the closing member 6 is a separate closing member 6 positioned in an opening of the upper part 1b of the housing, the opening in the housing will form a guiding rim for the finger, which will facilitate correct positioning of the finger during closure.

The closing member 6 is preferably made of a hard, non-flexible material preventing the closing member 6 from deforming and instead enabling the closing member 6 to react instantly to an applied force. The applied force enabling the closing member 6 to be activated to close the communication between said at least one inlet 7, 8 and said at least one outlet 12. Accordingly, it may be possible to achieve a closing action of the breathing protector by applying a low force. The upper part 1b of the housing is preferably also made of a hard, non-flexible material preventing the upper part 1b of the housing from deforming. This may protect the internal structure of the breathing protector and may further prevent any unnecessary pressure to be applied to the air filter 4. Further, it creates a strong and sealed snap-fit which facilitates manufacturing of the device.

As illustrated in FIG. 1, the housing of the breathing protector further houses a closing valve 10 arranged above the lower part 1*b* of the housing, wherein a first opening 11 is provided between the closing valve 10 and the lower part 1*b* of the housing. The closing valve 10 is thus arranged above, i.e. distally of, the HME 3, but below, i.e. proximally of, the air filter 4. Accordingly, when air passes from the surroundings through the stoma into trachea, air first enters into the housing via the at least one first inlet 7, 8 of the upper part 1*a* of the housing, through the air filter 4, through the first opening 11 and then through the HME 3 into trachea through the at least one outlet 12 of the lower part 1*b* of the housing. The closing member 6 is activated through an applied force in a proximal direction, i.e. in a direction towards the user. The force in the proximal direction will then move the closing valve 10 in the same proximal direction, until it reaches a closing valve seat 2, where after the closing valve 10 seals against the closing valve seat 2 and closes the communication between the at least one inlet 7, 8 and the at least one outlet 12.

In one embodiment, the closing member 6 is connected to the closing valve 10. The closing member 6 illustrated in FIG. 1 is connected to the closing valve 10 by reaching through the air filter 4. The closing member 6 is then provided with a protrusion 13. The protrusion 13 is arranged centrally of the closing member 6, and extends in the proximal direction. At the proximal end of the protrusion 13, the protrusion 13 is provided with hooks that may snap-fit into an opening 14 in the closing valve 10, proximally of the air filter 4. The air filter 4 is sealably fixed to the closing valve 10 and the closing member 6. In this way, the filtering effect provided by the air filter 4 may be kept high, while allowing for a reliable closing mechanism of the breathing protector. Also, the breathing protector may be closed by activating the closing member 6, which activates the closing valve 10, but without squeezing the air filter 4.

Accordingly, the closing member 6 is arranged to cooperate with the closing valve 10 during activation in order to close the communication between the at least one inlet 7, 8 and the at least one outlet 12 of the housing of the breathing protector. The closing effect may be obtained when the closing valve 10 closes the first opening 11. The proposed embodiment provides a breathing protector that builds more in height than on the diameter, which results in a more compact design. A more compact design may be advantageous as a larger user population generally accepts these. Furthermore, the proposed embodiment provides the possibility for a patient to close the breathing protector, such as during speech, with a low force. The structure of the disclosed breathing protector, with an externally accessible closing member 6, provides a distinct and well-defined closing while still providing a breathing protector with an air filter 4. The structure of the breathing protector provides tactile confirmation of a closing state, i.e. an open or a closed state, of the breathing protector.

The lower part 1*b* of the housing is provided with a closing valve seat 2, surrounding said HME 3. The structure of the closing member 6 and the closing valve 10 allows the closing valve 10 to be pressed down, inwardly, to closingly fit with the closing valve seat 2 of the lower part 1*b* of the housing, when the closing member 6 is pressed proximally, i.e. towards the user of the breathing protector. A closing effect is obtained when the closing valve 10 is pressed against the closing valve seat 2, such that the first opening 11 is closed and not allowing air to pass through the first opening 11. By achieving closing action from pressing down the closing member 6 instead of blocking airflow by holding a finger on the filter of the filter breathing protector, the air filter may be relieved from undue contamination from the finger.

Figure 3:
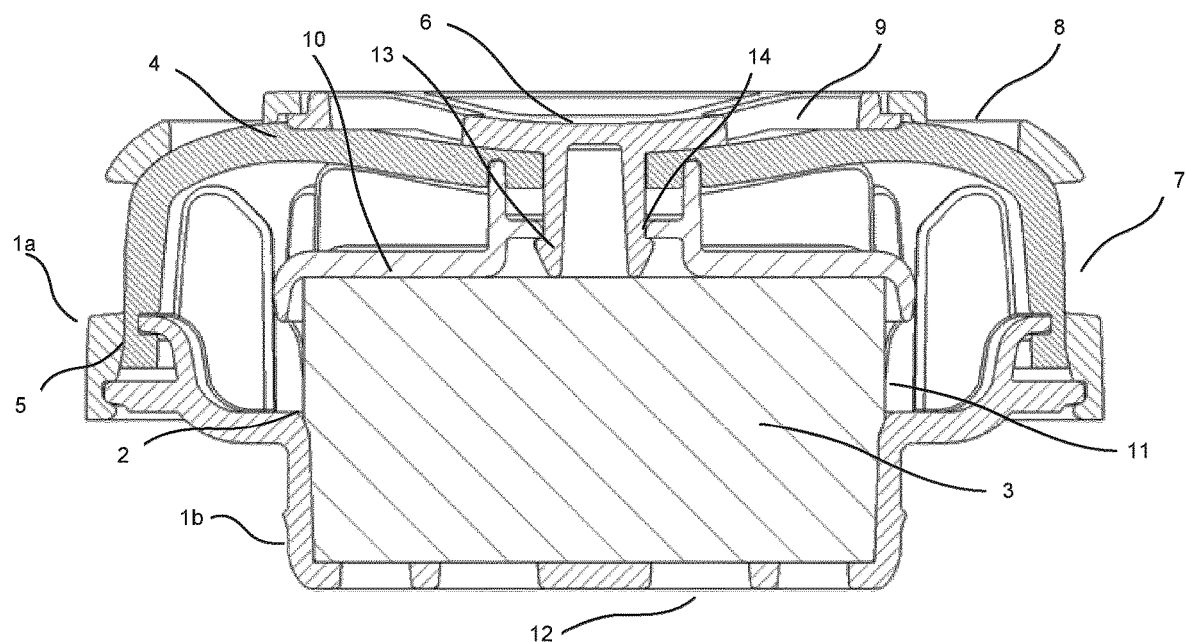
FIG. 3 is a cross sectional view of a breathing protector according to an embodiment of the present invention.
Figure 4:
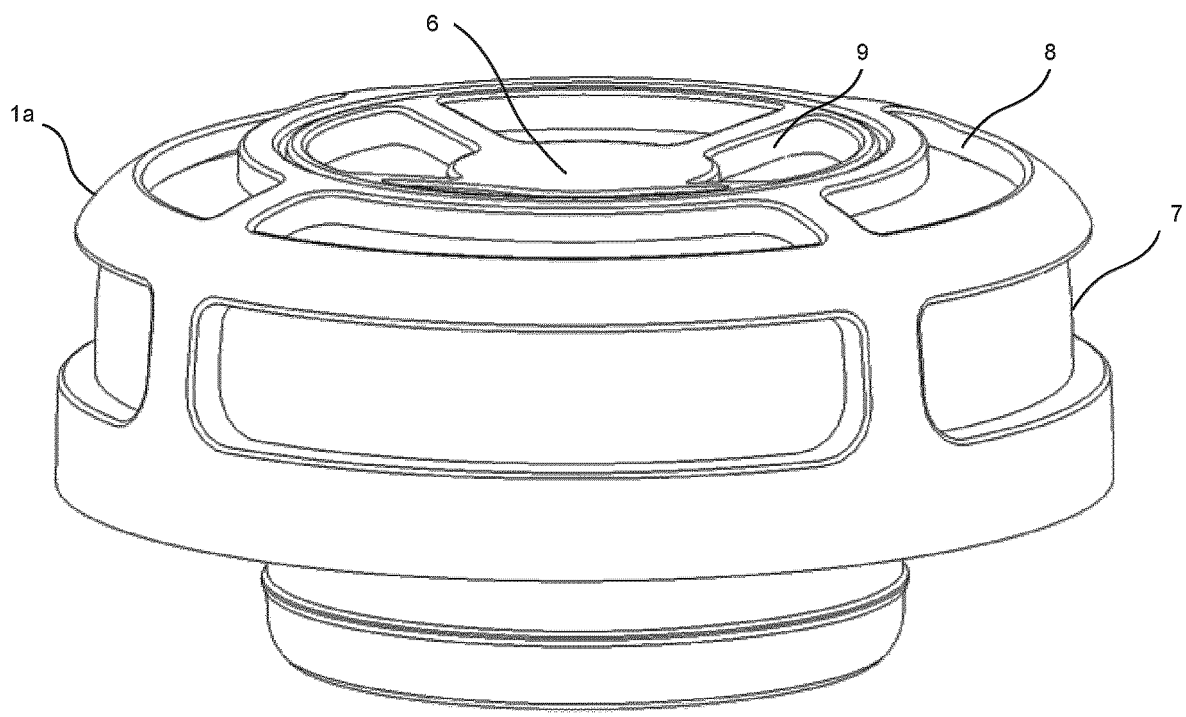
FIG. 4 is a perspective view of a breathing protector according to an embodiment of the present invention.

In one embodiment, as illustrated in FIGS. 3 and 4, the closing member 6 is provided with at least one inlet 9. Thus, the filtering area, provided by said air filter 4 may be increased as air may flow into the breathing protector through a larger number of inlets and thus providing the breathing protector with a larger inlet surface area. This may in turn decrease the resistance to airflow through the device, improving the overall functionality of the breathing protector, thus making the device more tolerable for the user during heavy breathing.

The air filter 4 is arranged in a three-dimensional structure with respect to the first opening 11. Thus, the filtering effect, provided by said air filter 4, is obtained in more than one dimension. In this way the filtering effect may be obtained in a large surface area while still providing the possibility to keep the size of the breathing protector small. Thus, the breathing protector may be kept from being bulky to the person wearing the breathing protector, while still providing a maximum filtering effect. The term "three-dimensional structure" is not intended to be limited to several sheets or layers, but is rather intended to illustrate a three-dimensional structure in contrast to a two-dimensional structure, such as a planar sheet or layer. Thus, the thickness of such a planar sheet or layer is not considered to be a three-dimensional structure in this respect.

The air filter 4, according to the embodiment disclosed in FIG. 1, is arranged in a three-dimensional structure with respect to the first opening by clamping the air filter 4 between a rim 5 and the lower/proximal housing part 1*b*. This rim 5 may have a substantially circular or ring shape. Thus, the air filter 4 then covering the cross section area of the rim 5, i.e. extending from the outer edges of the rim 5 to the opposite outer edges of the rim 5. The air filter 4 may thus be arranged to enclose the closing valve 10 within the housing, such that the air filter 4 will have a larger surface area than the area of the first opening 11 between the closing valve 10 and the lower part 1*b* of the housing. In this respect, the term surface area is not intended to include porosity of the air filter 4, but merely the outer area of the air filter 4, i.e. the circumferential area of the air filter 4. Effective area is instead used to define the surface area including the porosity of the air filter 4. In this way the effective area of the air filter 4 may be increased by the three-dimensional structure without increasing the pressure drop over the air filter 4, while only being limited by the cross section area of the rim 5 in respect of the size of the breathing protector. This increase in effective area, while only being limited by the cross section area of the rim 5, provides a high filtration efficiency such as more than 95%.

In another embodiment of the present invention the air filter 4 is pleated, folded, curved, arched, or in other ways provided with a three-dimensional structure, to provide a maximized filtering effect in a smaller size of the breathing protector.

The material of the HME 3 should include flow passages therein, and should have an open structure in which the flow passages are randomly oriented. The material may comprise paper, foamed plastics, wadding made of different fibres, or combinations thereof. It may also be impregnated with a moisture absorbing substance. Furthermore, it is advantageous if the pores or interstices in the material do not have any special direction, such that the breathing air easily may pass through the material in a number of directions in order to achieve the intended deflection.

In one advantageous embodiment, the material of the HME 3 may be a HME foam. In such embodiments, the HME 3 may additionally functioning as a return spring for the closing valve 10. The resiliency of the HME foam allows the closing valve 10 to return to an open state of the breathing protector when pressure thereupon ceases. Thus, the user may press the closing member 6 to close the first opening 11 by said closing valve 10. Then the user may turn the breathing protector into a speaking mode/state, when the user wishes to speak, and simply release the pressure on the closing member 6 when the user wants to quit speaking and returning breathing protector into breathing mode/state.

In the embodiments described above, a breathing protector for use in a stoma of a laryngectomized or tracheotomised person has been described. This breathing protector is configured with at least one inlet 7, 8, 9 and at least one outlet 12, such that an air flow in use will pass from the surroundings of said person through said inlet to said outlet 12, into trachea of said person. It is obvious to the skilled artisan, even if it has not been specifically disclosed, that the inlets and outlets may be divided into an increased amount by merely dividing the specific inlets and outlets already disclosed. Furthermore, this breathing protector comprises a HME 3 and an air filter 4, such that said air flow will pass through said HME 3 and said air filter 4 when said air flow in use passes through said inlet 7, 8, 9 to said outlet 12. Also, the breathing protector, according to the disclosures above, comprises a closing member 6 that may be activated to close the communication between said at least one inlet 7, 8, 9 and said at least one outlet 12.

According to one aspect of the present disclosure, there is provided a method for humidifying and filtering off bacteriological matter, during breathing through a stoma of a laryngectomised or tracheotomised person. The method comprises passing air from the surroundings into trachea of said person through a breathing protector having a housing with an upper part 1a comprising at least one inlet 7, 8 and with a lower part 1b comprising at least one outlet 12. The breathing protector comprises a HME 3 and an air filter 4. The method filtering off bacteriological matter by passing the air through the air filter 4. The air filter 4 have a surface area which is being larger than an area enclosed by the at least one inlet 7, 8. Thereafter, the method comprises moisturizing the air when the air is passed through the HME 3.

In another aspect, the present disclosure provides a method for closing a breathing protector for use in a stoma of a laryngectomised or tracheotomised person. The breathing protector have a housing, which comprises of an upper part 1a and a lower part 1b. The upper part 1a of the housing is provided with at least one inlet 7, 8 and the lower part 1b of the housing is provided with at least one outlet 12, such that an air flow in use will pass from the surroundings of said person through the at least one inlet 7, 8 to the at least one outlet 12, into trachea of said person. The breathing protector comprises a HME 3 and an air filter 4. The air filter 4 encloses the at least one inlet 7, 8, such that said air flow will pass through the HME 3 and the air filter 4 when said air flow in use passes through the at least one inlet 7, 8 to the at least one outlet 12. The upper part 1a of the housing further comprises a closing member 6 connected to a closing valve 10 arranged above, i.e. distally of, the lower part 1b of the housing. A first opening 11 is then provided between the closing valve 10 and the lower part 1b of the housing. The method comprises closing the first opening 11 by pressing the closing member 6 onto the lower part 1b of the housing.

The elements and components of the embodiments of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A breathing protector for a laryngectomized or tracheotomised person, the breathing protector comprising:
    a housing including an upper part coupled to a lower part;
    a heat and moisture exchanger (HME) and an air filter retained between the upper part and the lower part of the housing;
    a closing valve retained inside of the housing and located proximal the air filter and distal the HME;
    an opening formed in the upper part of the housing to form a guide rim on an exterior surface of the upper part of the housing;
    a closing member separate from the upper part of the housing, with the closing member inserted into the opening and exposed on the exterior surface of the upper part of the housing within the guide rim, with the closing member coupled to the closing valve;
    at least one inlet formed through the exterior surface of the upper part of the housing between the closing member and a side wall of the upper part of the housing; and
    at least one outlet formed through the lower part of the housing such that air flow, during use, passes into the at least one inlet and out of the at least one outlet and into a trachea of the person;
    wherein the closing member is movable within the opening in an axial direction toward the HME to close the air flow between the at least one inlet and the at least one outlet.

2. The breathing protector according to claim 1, wherein the HME is arranged in the lower part of the housing.

3. The breathing protector according to claim 1, wherein the air filter is arranged in the upper part of the housing.

4. The breathing protector according to claim 1, wherein the air filter is an electrostatic filter.

5. The breathing protector according to claim 1, further comprising at least a second ais inlet formed in the closing member and located within an area of the guide rim.

6. The breathing protector according to claim 5, further comprising at least a third air inlet formed in the side wall of the upper part of the housing.

7. The breathing protector according to claim 6, further comprising at least a fourth es inlet provided between the closing valve and the lower part of the housing.

8. The breathing protector according to claim 7, wherein the closing member is provided with a protrusion arranged centrally of the closing member and the protrusion is provided with hooks at a proximal end of the protrusion, wherein the hooks of the protrusion snap-fit into an opening in the closing valve.

9. The breathing protector according to claim 7, wherein the closing member during activation is arranged to cooperate with the closing valve to close the air flow through the fourth air inlet provided between the closing valve and the lower part of the housing.

10. The breathing protector according to claim 7, wherein the HME comprises a foam.

11. The breathing protector according to claim 10, wherein the foam is structured and arranged to act as a return spring for the closing valve.

12. The breathing protector according to claim 1, wherein an outer periphery of the closing member projects through the guide rim and an outermost perimeter of the closing member is retained under the guide rim within the opening of the upper part of the housing.

13. The breathing protector according to claim 1, wherein the air filter is a pleated three-dimensional structure.

14. The breathing protector according to claim 1, wherein the air filter is a folded three-dimensional structure.

15. The breathing protector according to claim 1, further comprising a rim having a circumference of said lower part of the housing, the air filter being attached to the rim, wherein the air filter covers a cross section area of the rim, and wherein the air filter is arranged in a three-dimensional structure.

16. The breathing protector according to claim 1, wherein the closing member projects through the opening and is exposed centrally within the upper part of the housing.

17. The breathing protector according to claim 1, wherein the guide rim on the upper part of the housing provides a guiding feature for positioning a user's finger relative to the closing member.

18. The breathing protector according to claim 1, wherein the at least one outlet is formed through the lower part of the housing and located opposite from the closing member.

19. The breathing protector according to claim 1, wherein the guide rim on the exterior surface of the upper part of the housing is located between the at least one inlet formed through the exterior surface of the upper part of the housing and the closing member.

20. The breathing protector according to claim 1, wherein the at least one inlet comprises a plurality of inlets formed through the exterior surface on a distal portion of the upper part of the housing between the closing member and the side wall of the upper part of the housing.

21. The breathing protector according to claim 1, wherein the at least one inlet comprises a first plurality of inlets formed through the exterior surface on a distal portion of the upper part of the housing between the closing member and the side wall of the upper part of the housing and a second plurality of inlets formed in the closing member and located within the area of the guide rim.

* * * * *